(12) United States Patent
Silva Ramos et al.

(10) Patent No.: US 10,449,033 B2
(45) Date of Patent: Oct. 22, 2019

(54) APPARATUS FOR AUTOMATED DIFFERENTIAL HAIR TRANSPLANT

(71) Applicant: COSMIKBALANCE LDA, Maia (PT)

(72) Inventors: Paulo Silva Ramos, Maia (PT); Fatima Cruz Funy Garces, Ponte do Rol (PT); José Almeida Gracio, Aveiro (PT); Abilio Ribeiro Borges, Oliveira do Bairro (PT); Carlos Madail De Sa Martins, Oliveira do Bairro (PT)

(73) Assignee: COSMIKBALANCE LDA, Maia (PT)

( * ) Notice: Subject to any disclaimer, the term of this patent is extended or adjusted under 35 U.S.C. 154(b) by 811 days.

(21) Appl. No.: 14/894,870

(22) PCT Filed: May 30, 2014

(86) PCT No.: PCT/IB2014/000910
§ 371 (c)(1),
(2) Date: Mar. 21, 2016

(87) PCT Pub. No.: WO2014/191827
PCT Pub. Date: Dec. 4, 2014

(65) Prior Publication Data
US 2016/0193035 A1 Jul. 7, 2016

(30) Foreign Application Priority Data

May 30, 2013 (PT) ........................................ 106977

(51) Int. Cl.
*A61F 2/10* (2006.01)
*A61B 17/34* (2006.01)
(Continued)

(52) U.S. Cl.
CPC ............ *A61F 2/10* (2013.01); *A61B 17/3468* (2013.01); *A61B 34/30* (2016.02); *A61B 2017/00752* (2013.01); *A61B 2017/00969* (2013.01)

(58) Field of Classification Search
CPC ........... A61B 2017/00752; A61B 2017/00969; A61B 34/30; A61B 17/3468
(Continued)

(56) References Cited

U.S. PATENT DOCUMENTS

| 5,908,417 | A | 7/1999 | Miller et al. |
| 5,951,572 | A | 9/1999 | Markman |

(Continued)

FOREIGN PATENT DOCUMENTS

| AU | 2011250755 | 12/2011 |
| AU | 2012203687 | 7/2012 |

(Continued)

OTHER PUBLICATIONS

International Search Report and International Preliminary Report on Patentability dated Sep. 11, 2014 in corresponding International Patent Application No. PCT/IB2014/000910.

(Continued)

*Primary Examiner* — Diane D Yabut
*Assistant Examiner* — Majid Jamialahmadi
(74) *Attorney, Agent, or Firm* — B. Aaron Schulman, Esq.; Stites & Harbison, PLLC

(57) ABSTRACT

The present invention relates to an apparatus for automated hair transplantation through the well-known extraction technique of capillary units or FUE, comprising the morphological analysis of hair follicles in real-time by means of artificial vision, mapping of points for extraction and implant, simulation of the final result, a system of local anaesthesia, global, simultaneous or in sequential phases, at (Continued)

least one articulated mechanical arm associated with a tool for differentially extracting and implanting hair follicles.

The present invention is useful to reduce the time and cost associated with the intervention, improve the quality of the operation and the final result, in terms of capillary density, contemplating the study of cell differentiation of follicles with the required estimate of time required regarding the growth. Minimizes the positional discomfort of the patient, the pain associated with the administration of anaesthesia, among other inconveniences usually experienced by the patient in this type of intervention. The present invention is useful for diagnosis, treatment and hair transplantation procedures.

14 Claims, 12 Drawing Sheets

(51) Int. Cl.
*A61B 34/30* (2016.01)
*A61B 17/00* (2006.01)

(58) Field of Classification Search
USPC .................................. 606/133, 187; 604/7.8
See application file for complete search history.

(56) References Cited

U.S. PATENT DOCUMENTS

| 6,027,512 | A | 2/2000 | Bridges |
| 2002/0103500 | A1* | 8/2002 | Gildenberg ...... A61B 17/32053 606/187 |
| 2007/0078473 | A1 | 4/2007 | Bodduluri et al. |
| 2007/0106306 | A1* | 5/2007 | Bodduluri ......... A61B 17/32053 606/133 |
| 2007/0106307 | A1 | 5/2007 | Bodduluri et al. |
| 2008/0167674 | A1 | 7/2008 | Bodduluri et al. |
| 2008/0167750 | A1* | 7/2008 | Stahler ............. A61B 17/12122 700/245 |
| 2008/0183110 | A1* | 7/2008 | Davenport ............... A61N 7/02 601/3 |
| 2010/0179580 | A1 | 7/2010 | Oostman et al. |

FOREIGN PATENT DOCUMENTS

| JP | 2010279714 | 12/2010 |
| WO | WO-00/64379 | 11/2000 |
| WO | WO 2007/041267 | 4/2007 |
| WO | WO-2014/191827 | 12/2014 |

OTHER PUBLICATIONS

Written Opinion dated Sep. 11, 2014 in corresponding International Patent Application No. PCT/IB2014/000910.
Written Opinion dated Oct. 17, 2013 in corresponding Portuguese Application No. 106977.

* cited by examiner

APPARATUS FOR AUTOMATED DIFFERENTIAL HAIR TRANSPLANT

TECHNICAL FIELD OF THE INVENTION

The present invention relates to an automated apparatus for hair transplantation through the extraction of follicular units or FUE (Follicular Unit Extraction), comprising: 1) Pre-analysis for simulation of the end result, through a computerized interface for online use e.g. via skype and morphological analysis of hair follicles in real time, through artificial vision; 2) system of local anaesthesia, global, simultaneous or phased; 3) excision, selection and differentiated implantation of multiple follicles, preferably between 1 and 100 follicles.

SUMMARY OF THE INVENTION

The present invention relates to an apparatus for automated hair transplantation through the extraction technique of follicular units or FUE, comprising a phase of pre-analysis, mapping extraction and implantation points, the simulation of the final result, and selecting the follicles in real time with a 1) computerized interface for online use and morphological analysis of hair follicles, through artificial vision; 2) system of local, global, simultaneous or phased anaesthesia; 3) excision, selection and sequential implantation of multiple follicles, preferably between 1 and 100 follicles, wherein those follicles are differentiated when excised and implanted or eliminated, according to its morphology and type (containing 1, 2 or 3 hairs).

Thus the present invention is useful to significantly reduce the time and expenses associated with the procedure, both in terms of the necessary resources, such as the number of people involved, allowing a prior differentiated assessment of the viability of the follicles to be used in the procedure and allowing the screening thereof during the procedure, significantly improving the outcome and minimizing the discomfort, pain and other inconvenience to the patient, such as for example the need to perform this type of intervention in several phases, with a distribution and time intervals to long, wherein this problem is considerably minimized by using the present invention.

Currently, the administration of anaesthesia, usually a painful and time-consuming process—on an area with about 180 cm2, needs about 78 mL of diluted anaesthesia, using a syringe of 3 mL to perform about 20 sequential and isolated administrations, which are usually painful and slow. The time elapsing between administration of anaesthesia and the moment from which it's effect starts can be about 30 minutes. With the present invention, this period can be reduced by approximately 10 to 40%.

The risk of non-survival of the follicles resulting from the period of anoxia due to absence of vascularization, reduces dramatically during the waiting time for the implantation with the present invention. This is achieved through the simultaneous use of between 1 and 100 needles of excision located in the tool associated with, at least, one mechanical arm.

The present invention is applicable in the area of diagnosis, treatment and hair transplantation, particularly in what regards the improvement of the final result of the hair transplant through the extraction technique of follicular units (FUE).

STATE OF THE ART

Document U.S. Pat. No. 5,908,417 discloses a method for hair transplantation using laser technology, which methodology differs from that used in the present invention, the latest being based on the extraction of follicular units (FUE) (Follicular Unit Extraction), resulting in a safe treatment from the point of view of their effects on the health of the patient and the duration of which is at least as low as the duration of the treatment with laser and the cost involved for the patients is considerably reduced compared to all other techniques currently used in the field of hair transplantation.

Documents WO0064379 and US2002103500A1 disclose a technique for transplantation of, at least, one follicle of hair using also a stereotactic robot, which includes an arm having associated an introducer of follicles that can be a multi-needle system, which can allow the insertion of multiple follicles within the scalp. They also disclose the possibility of using rotating heads in the robotic arm for the introduction of the follicles with the correct orientation, being the coordinates calculated by means of a video system associated with the equipment. This disclosure does not provide, however, for the morphological differentiation of follicles in the excision and implantation. This functionality is comprised within the scope of the present invention.

Documents US2007/106306A1, US2007/106307A1 and WO2007041267A2 disclose an automated system containing a needle with triple functionality and method for incision, harvesting and implantation, wherein each of its 3 elements moves independently from the other 2. It also contains two or more video cameras associated with the robotic arm with a processor configured to receive and process the images captured by these cameras and based on the information collected by these images it conceives a treatment plan including the transplantation of follicles from the donor area to the receiving area, however with an associated degree of randomness that makes it impossible to estimate in advance the amount of follicles needed to transplant to the receiving area or to calculate the quantity of viable follicles available in the donor area of the patient, as it is provided by the present invention.

Documents BR 0616648 A2 and JP 2010279714 disclose a robotic system image-guided, used to harvest and implant, in a precise and controlled manner, follicular units of hair. In some embodiments, the system includes a movable arm, an instrument mounted on a movable arm, and one or more cameras. In the present invention it is important to point out that the system of automated extraction and the vision system will operate in an integrated manner, allowing to simultaneously remove a large number of follicles (preferably between 1 and 100) and proceed to its morphological differentiated separation, depending on the follicle containing 1, 2 or 3 hairs, or if the follicle does not comply with the minimum requirements established for the hair transplant regarding morphology and viability, it is rejected and subsequently discarded. There is also to consider the simplified procedure for automatic routing of these follicles to the needles of implantation, being this also differentiated by type of follicle (for example, in the case of the embodiment of the invention comprising two mechanical arms). Similarly, the implantation system has incorporated therein the information regarding the number of follicles containing 1, 2 or 3 hairs, to implant and what are the respective regions for implantation. Thus, the differentiated morphological organization of follicles in the visualization system and in the implantation system, together with the ability of the robotic head to implant up to 100 follicles simultaneously, will allow a significant reduction in the duration of the hair transplant intervention.

Document US2007078473A1 discloses a mechanism of follicular extraction which consists of an internal cannula for collection of the follicles and an external concentric cannula for puncturing the patient's skin; in a given embodiment of the present invention, it may have dual function of extraction and implantation; during extraction both cannulas are aligned preferentially with axial orientation among them. The multi-part device can be assembled on a robotic arm. In a given embodiment of the present invention, a skin incision is made by 1 to 100 needles at the same time, wherein the excision of the follicle is accomplished with a cylindrical hollow tube or cannula with 0.75, 0.80 or 1.0 mm in diameter, with suction/aspiration capacity through multiple channels and the routing of the follicles is performed directly and differentially to the channels of implantation and up to 100 follicles can be implanted simultaneously.

Document US2008167674A1 discloses similar methods to those described previously in the state of the art regarding the extraction technique of follicular units (FUE), automated or not, but with different purposes from those of the present invention, being the main purpose the distribution of chemical substances and/or drugs in the patient's body. This document also discloses the use of substances that promote the growth and development of follicles. In the latter context, comparatively, the pre-transplantation system used in the present invention provides for two distinct approaches. The first approach, with a mechanical character, determines the number of differentiated follicles needed to repair the area of baldness to be intervened; the second approach, with biological character, encompasses the study of morphological differentiation, with the aim of selecting for extraction only follicles in the growth phase, which have—ideally— approximately 0.6 mm in diameter.

Document US2010179580 discloses a mechanism for implanting hair follicles and ensures that, during implantation, the previously implanted follicular units do not "pop out"; this mechanism is based on combining a notch whose diameter covers the area immediately surrounding the area of implant and acts mechanically, by exerting direct pressure on this area. The present invention provides for this functionality by controlling the pressure associated with the extraction and implantation tool, which has advantages due to two distinct factors: 1) the skin puncturing by the needle or the tube to perform the implant is held gently with the aid of a peristaltic valve and 2) the reduction of tissue swelling, as a consequence from the application of anaesthesia simultaneously in multiple different locations and to a lesser amount, will improve significantly the outcome of the intervention, facilitating the penetration of extraction tool of follicles into the skin of the patient's scalp, and preventing the pop out of implanted follicles.

Document AU 2011250755 A1 discloses an automated system for collecting or implanting hair follicular units, including an articulated arm; extraction and/or implant tool assembled on a articulated arm; one or more cameras mounted on the articulated arm; processor configured to receive and process images acquired through one or more cameras; controller operationally associated to the processor and configured to position the articulated arm based, at least in part, on the acquired processed images wherein the articulated arm is manipulated in a way that the tool can be positioned with the desired orientation with respect to a body surface. Although reference is made to the extraction of at least one follicle, this document does not disclose the possibility of simultaneously extracting up to 100 follicles nor the capacity of this extraction being differentiated and associated to an implantation system of the hair follicles, also differentiated by the type of follicle (containing 1, 2, 3 or more hairs), according to the present invention.

Document AU2012203687 discloses a system and method for excision, storage and implantation of follicular units, wherein at the time of excision, an analysis and typing of follicle are made, directing them to the corresponding individual storage receptacles and maintaining the registration of some information regarding these hair follicles, in particular, their number, size, type and nature. This document also mentions that the path traversed by the hair follicular unit comprises an open channel through the tool of excision and that the system includes the means for creating a pressure differential in this channel to promote the transfer of the follicle through it. In addition, this document mentions the possibility of, after excision and typing, implanting the follicular units instead of the storing them. Although document AU2012203687 mentions the possibility to apply this system both manually and automatically, it does not explicitly refer to the possibility of multiple implant up to 100 follicles, and in addition does not contemplate the use of two mechanical arms independently, one for extraction and one for implantation of hair follicular units, without the need for temporary or permanent storage of these follicles, as is the case of the present invention, which also assesses the follicles regarding its biology and morphology, considerably reducing the time and efficacy of the transplant. The present invention also contemplates the use of three systems of artificial visualization in real-time that, in its whole, ensures the assessment and record of all information collected by the equipment disclosed in AU2012203687 and in addition to these, provide the possibility of doing—also in real-time—the selection of the excised follicles and their routing to the corresponding implantation tools, depending on its type, morphology and size, and in addition allows for the direct discard of the follicles assessed as non-viable for transplantation and also provides the predicted time required for hair growth and the elapsed period until it reaches the intended result and/or desired. In addition, and improving the patient's comfort, the two mechanical arms of one of the embodiments of the present invention, apply multiple micro- and/or nano-doses of anaesthesia, during the hair transplant procedure to cover only the intervened areas of the patient's head and to reduce the swelling and pain associated with the administration of this type of anaesthesia.

GENERAL DESCRIPTION OF THE INVENTION

The extraction technique of follicular units or FUE (Follicular Unit Extraction) consists in obtaining hair by extracting hair follicles from donor areas of the patient's scalp, and implanting them afterwards on the receiving area (bald area). According to the most common procedure in the state of the art, the follicles are usually extracted one by one and those which comply with a predefined set of specific morphological requirements and are considered to be viable for hair transplant, are placed in Petri dishes containing 0.9% NaCl solution, at 4-5° C. and subsequently implanted on the receiving area, without being damaged. There are, however, also automated technologies for extraction of follicular units (FUE), contemplating the sequential extraction and implantation of the follicles in a way wholly or partially automated, already detailed in some documents mentioned in the previous section.

The FUE technique of hair transplantation allows us to obtain individual, double, triple or quadruple follicles, according to the specific needs of each patient, without causing trauma, because there are neither sutures nor scars resulting from this process. A small incision is made with maximum diameter of 1 mm when the extraction of each follicular unit is performed. It takes usually 3 to 4 days for the cicatrisation to occur and the resorption of the face edema is complete usually up to 7 days after the hair transplant procedure. The patient returns home on the same day.

This is a painless procedure, being carried out with the use of local anaesthesia and allowing also the transplant of body hair for small areas of low capillary density or without hair. This technique is useful for patients with a donor area considered as being "good" (with more than 15 follicles per $cm^2$); "reasonable" (with 10 to 15 follicles per $cm^2$) and "bad" (less than 10 follicles per $cm^2$). Each intervention usually takes about 6 hours, being possible to interrupt for brief periods of time and resume the procedure or to perform the treatment in different stages, encompassing more than one intervention. It is strongly recommended to transplant the excised follicles within a maximum period of 9 hours from the time of the extraction of the first follicle, to preserve their integrity and viability.

By means of this technique a large number of follicles can be transplanted, having a maximum limit corresponding to the maximum amount of follicles possible to transplant during a period of 9 hours. The clinic Saúde Viável® has a long track record of hair transplant procedures, transplanting, in average, 1,250 follicles in each intervention, and in some patients transplanted more than 1,500 follicles—one by one—something like 3,000 hairs, since each one of these follicles may contain between 1 to 4 hairs and rarely 5. The transplanted hairs are very short and usually fall off within the first three months after the intervention due to the renewal of the apical section or rod. The hair root produces a new hair that will grow with normal texture and thickness. Once transplanted, the follicles will continue to produce hair as they use to do in the area from where they were removed.

These transplanted hairs are not subsequently influenced by DHT (di-hydrotestosterone) metabolism and, therefore, are less likely to fall off due to this hormone.

Being this procedure performed with hair from the same patient, the risk of rejection is thus minimized or even eliminated, and the final result is a natural look, very different from the image attained by using a wig or other artificial solutions.

There are other widely used techniques in hair transplantation, in particular Laser and Strip, all of which have advantages and disadvantages regarding the extraction technique of follicular units (FUE) currently used (Table 1).

TABLE 1

Comparison of the most commonly used techniques of hair transplantation

| DESCRIPTION | STRIP | FUE | LASER |
|---|---|---|---|
| Removal of follicular units | Removal of a tissue strip containing the necessary follicular units | Extraction of Follicular Units, one by one | Not used in the donor area |
| Anaesthesia | Like in FUE and LASER | Like in STRIP and LASER | Like in STRIP and FUE |
| Experienced Pain after intervention | Occurring | Non-occurring or bearable | Non-occurring or bearable |
| Covers large areas | Very Good | Very Good | Very Good |
| Covers small areas | Very Good | Excellent | Excellent |
| scar in the donor area | Linear scar | Absence of scar | Not used in the donor area |
| Treatment Time | Medium | Long | Short |
| Loss of follicles during extraction | Small | Medium | Not used in the donor area |
| Appearance of donor area at the end of treatment | Invisible with grown hair | Invisible with grown hair | Invisible with grown hair |
| Incisions in the receiving area for implantation of follicular units | Puncture device or tool | FUE Implantation device or tool | Laser Light |

Despite the advantages of laser technique in terms of the length of time of intervention and the time for recovery, in addition to the fact that the capillary density obtained can be higher than that obtained by the other two techniques mentioned, conclusions have not yet been obtained regarding safety in the use of laser for hair transplantation and even in relation to the effects it may have on the health of the patient.

Therefore, a need arises for a technology that allows the performance of capillary transplantation in a manner that is fully automated and safe to the patient, that is fast, with reduced costs for clinics and patients, involving not only a stage of pre-analysis prior to the intervention, in which the planning of the intervention is performed, contemplating a degree of detail not achieved until now through the technologies available and also an anaesthesia in at least two different locations, with a mechanism for controlling the pressure in order to prevent the unnecessary pressure that usually occurs after the administration of anaesthesia. Alternatively, the anaesthesia can also be applied in a progressive mode, throughout the intervention. It can even be adopted an intermediate procedure, combining anaesthesia across multiple locations and reinforcement on certain areas of the patient's head, in the course of the hair transplant procedure or intervention.

The observed tissue swelling after administration of anaesthesia is useful during the manual extraction of the follicles, which provides rigidity to the surface of the skin, making easier to cut the skin and isolate the follicle. The absence of a proper swelling in the area of extraction, when manual extraction is performed, requires a higher pressure ejector to isolate the follicle.

With the apparatus of the present invention, the applied anaesthesia covers the entire intervened region, with multiple simultaneous and/or progressive administrations, with the advantage of causing less swelling comparatively to the manual procedure, because the automated extraction does not need these conditions to ensure an effective extraction of the follicles. In addition, the experienced pain in the post-operative period by the patient is also considerably reduced.

The phenomenon known as hair follicle "pop-up" consists of the unwanted full output of recently implanted follicles and can be caused by 2 or more factors acting together, in particular in the presence of:

a) An area of difficult haemostasis—sometimes happens in young, healthy patients, without coagulation or signs of liver function changes.
b) Skin with low elasticity—often being a innate characteristic, although it can also be due to the presence of scarred tissue after a previous "strip" intervention or other traumas.
c) High volume of local anaesthesia.

This phenomenon, when originated by one or more of these factors, can be avoided by:
1—Lower quantity of local anaesthesia.
2—Controlled bleeding;
3—Implantation after the beginning of coagulation, with evidence of clots, when the performed incisions are less slack because they contain multiple connections narrowing the holes.

All of these conditions are ensured through the use of the apparatus of the present invention.

The capillary transplantation consists in effectively extracting and harvesting hair follicles from a donor area to implant in the receiving area. Generally, donor areas are located in the neck region and sides over the ears, because these areas are not affected by male pattern baldness. The hair characteristics in different donor areas are important to determine the number of hairs in a given structure to be excised and implanted on a given receiving area. For example, the thicker follicles are located in the "neck" and usually the majority contains 2, 3, or hairs and rarely 5. These follicles, having a larger structure, are implanted in the "crown" area and on the top of the patient's head. The hair follicles containing only one hair are implanted preferably on the front line area of the patient's head (FIG. 9).

Another important consideration in the planning of extraction is that the permanent fall of hair will continue subsequently and gradually during some years after the intervention. Therefore hairs from the donor area should be kept for future transplants. The selected follicles for extraction should be removed in an alternate or discontinued manner. Once placed in the receiving area, they will continue to grow, providing coverage to other areas that lost hair.

Other Techniques of Follicular Extraction

"STRIP" is a classic technique for hair follicles removal, in which a single, double or triple scalpel is used to remove a strip of skin containing hair, from the donor area. On a later stage, hair follicles are dissected from the strip of skin, ready to be implanted. The hair follicular units can be individualized or grouped. The incisions made to remove the strip are closed with sutures or staples.

The strip by extraction elliptical is a variant of the previous one, in which the incision to harvest strip has an oval elongated.

The graft extraction is a technique practically in disuse, wherein large groups of grouped follicles are removed in round sections, with a punch of 3-5 mm and implanted without separation of follicular units.

Life Cycle of the Follicle

During its lifetime, all hair follicles go through between 10 to 20 times the Anagen-Catagen-Telogen cycles. At any time about 1% of the hair follicles are in the catagen phase (degradation), around 15% in telogen phase (dormant) and 84% in anagen phase (growth). In a stage prior to extraction, the hairs should be evaluated in terms of their biochemical structure, which defines the phase of the cycle they are at the time. They are elected as being able to transplant the hair whose structures are in the anagen phase or growth phase.

The terminal hairs are thick (up to 0.6 mm). When they finish their anagen phase the matrix cells stop to divide and the growth is stopped. They enter the catagen phase during 2-3 weeks and the matrix cells are fully keratinized. The next phase is the telogen or dormant phase and eventual hair fall. The androgens bind to receptors in the cytoplasm and nucleus of the cells of the dermal papilla and some cells of the sheaths of the follicle, but only if the hair is on anagen or telogen phase.

The germ cells of the hair follicle are grouped in the basal layer of the projection of the outer sheath of the hair root. The matrix cells are formed from these cells. The growth and differentiation of matrix cells are under the influence of substances produced by the cells of the dermal papilla. On the other hand, the secretory activity of dermal papilla is controlled both by substances produced in the cells of the stratum spinosum of the external sheath of the hair root or by hormones. The cells of the stratum spinosum produce peptides of 3000 daltons or more, which increases the number of mitosis of papillary cells in two to five times. It was recently discovered that the basic fibroblast growth factor (bFGF) and the platelet-derived growth factor (pDGF) improves the growth of dermal papilla cells. It has been proposed that these proteins increase the synthesis of stromelysine (an enzyme, matrix metalloproteinase), which operates in papillary cells and accelerates its growth. Another cytokine, beta transforming growth factor (FTC-$\beta$), inhibits the proliferation of cells of the dermal papilla induced by mitogens. On the other hand, the cells of the dermal papilla produce many cytokines that influence the proliferation of hair matrix cells. Some of these act by stimulating this proliferation, others by inhibiting. The interleukin 1 (IL-1) inhibits the growth of hair and follicle, but only after 2-4 days of latency. The increase in the concentration of IL-1$\alpha$ in the extracellular fluid during inflammation could be one of the reasons to explain the alopecia that follows certain infectious diseases. In addition to the participation of IL-1, both the fibroblast growth factor (FGF) and the epidermal growth factor (EGF) inhibit the growth of hair and hair follicle. The type 5 fibroblast growth factor (FGF5) is an especially powerful inhibitor. The receptors for these "ligands" were identified through immunohistochemical methods in papillary cells, matrix cells and germ cells in the region of the projection of the hair follicle. Another cytokine produced by the cells of the dermal papilla, the keratinocytes growth factor (KGF), induces a significant increase in hair growth on murinic models of alopecia. Receptors were identified for these KGF in keratinocytes of the basal epidermis and along hair follicles in developing embryos and neonates of mice. The insulin-like growth factor I (IGF-I) accelerates, in a manner dependent on the concentration, the hair growth and hair follicles. The actions of IGF-I are modulated by proteins produced in the cells of the dermal papilla that bind to IGF (ligand proteins of insulin-like growth factor I: PLFCI); the exact mechanism of modulation has not yet been clarified. However, it has been demonstrated that the PLFCI-3 (which are the most abundant among PLFCI cells in the dermal papilla) form a complex with free IGF-1 to reduce the concentration of IGF-1 available for the stimulation of capillary elongation and maintenance of anagen phase. The retinoids and glucocorticoids stimulate the production of PLFCI-3 in the cells of the dermal papilla. Insulin itself has the same effect as IGF-1; it has been observed that the body hair in patients with hyperinsulinism has a distribution pattern in males. The substances regulating the homeostasis of calcium and phosphorus may also be involved in the control mechanism of hair growth. The parathyroid hormone (PTH) and the corresponding peptide PTH inhibit hair growth and the proliferation of epidermal cells. 1,25-hydroxyvitamin D3 (1,25/OH/D3) when in low concentration (1-10 nM) stimulates, and when in a higher concentration (100 nM) and after a longer contact period inhibits hair and hair follicle growth. These actions from PTH and from 1.25/OH/D3 require direct contact with hair follicles. In the universe of all androgens, cells of the dermal papilla are more affected by 5-αdi-hydrotestosterone (5α-DHT). This is synthesized in these cells from testosterone under the catalytic action of the enzyme 5-α-reductase type II.

Differentiated Hair Transplant

The apparatus for extraction, selection and implantation of hair follicles of the present invention allows the individual adjustment of the positioning and orientation of the patient's head, allowing a pre-adjustment according to the area and density of the hair follicles to be implanted. The angles and density of implantation are set automatically by the computer platform associated with the apparatus and adjusted according to the parameters evaluated by the responsible physician or technician. A 3D simulation is performed, visible on a monitor, for validation of the assumptions defined in the pre-assessment performed before the intervention.

In a preferred embodiment, one or more of the following supports is used with the system and apparatus of the present invention.

1) Rolling Bed or Chair with multiple positions (1) and design appropriate to the activity and the apparatus, allowing in particular the placement of the patient on Trendelenburg position, in order to facilitate the extraction and implantation of the hair follicles. The position may also vary in such a way as to increase the patient's comfort and reduce fatigue.

2) Simulator/Consultation Online and Presencial

The hair style and final result are simulated in 3D, according to the expectations of the patient, helping the doctor with mapping of points for extraction and implantation and indicating the number of follicles needed for transplantation and the section of origin for the same. This simulation is performed in the context of a live and/or online consultation (for example, via skype http://www.skype.com/pt/). The result of the simulation is very close to reality, as it is presented in 3D. An integration/synchronization is made online and the presented information is recorded.

3) System of Support on the Consultation for Initial Evaluation

Introduction and recording clinical data from the patient.
Photographs of the patient's head (donor areas and receiving areas) and other potentially donor areas.
Clock/Timer for monitoring the time of intervention/transplant procedure;
Recording and Registration of Data and Intended Results.

The system of pre-intervention evaluation included in the present invention provides for two distinct stages: The first—in the diagnostic phase—aims to determine the number of differentiated hair follicles necessary to repair the area of baldness where you want to intervene, in addition to identifying the causes of hair loss, serving as the basis for a second stage, which includes the study of cell growth and differentiation in order to give the patient a more accurate prediction time for the hair "regeneration".

Until now it was only possible to do this type of assessment at the time of extraction; however if the patient has the hair as short as possible at the time of preoperative evaluation, it is possible to predict at this time how many follicles of 1, 2, 3 or more hair the patient has in donor area and assess whether they are sufficient, and with greater precision and efficiency to predict the final result obtained after the transplant.

The visualization system used herein can also anticipate the morphological viability before incision, in order to select and intervene only in eligible areas. The criteria for selection of these eligible areas match the morphological characteristics of the hair rod, such as thickness, length, type of follicle, among others.

In the course of the development of the present invention, it is predicted the design and use of a mobile application compatible with the system and apparatus of the invention, for use in mobile devices, such as smartphones, tablets, among others, to carry out the consultation of pre-assessment.

Automated Apparatus for Hair Transplantation

The present invention includes an apparatus for sequential extraction, selection and implantation of hair follicles and a system of artificial vision in real time (2) which act in an integrated manner.

The system of external artificial vision on the upper part of the robot (FIG. 1), is equipped with: Laser Scanning, Time-of-Flight Chamber and a Conventional Camera, with the purpose of constructing a 3D map containing the points of extraction and implantation, the contours and dimensions of the head and the location of the follicles, allowing to identify the existing follicles in the scalp and remove them; the 3D map allows to further define the ideal paths to carry out by the robot in order to be correctly positioned in relation to the preferred follicles for extraction.

PREFERRED EMBODIMENTS

One of the embodiments of the present invention allows you to excise a large number of hair follicles (preferably up to 100) and proceed to its morphological screening (3), identifying follicles with 1, 2, 3 or more hair follicles or rejecting and automatically routing them to a density selector system (FIG. 2) (4), equipped with a system of artificial vision (2) that allows the identification and classification of the follicles and respective routing to, preferably 1 to 100, channels of implantation (6)—positioned adjacently to needles for puncturing the skin in implantation points defined by the 3D map—or to the deposit of rejected follicles (7), without the need for intermediate storage. This forwarding and displacement of hair follicles is performed through pressured channels (24), with an associated vacuum system. Each extraction tool has a hose (9) that connects to a capsule, from which the follicle is directed to the desired tool, located on the arm of implantation (15), using a preferred mode, a mechanical system that allows you to change the nozzle of the capsule (8), according to the procedure to perform, as illustrated on FIG. 3.

Cylindrical transparent and disposable capsules are used, preferably with 0.75, 0.80 or 1.0 mm in diameter (allowing to perform the analysis to the follicle in the intermediate point of the route, after being excised and before being implanted, preventing contamination of the follicles due to residues from previous interventions.

In FIG. 3 a tube is visible, which is derived from one of the extraction tools, connected to the capsule, with at least three outputs for each one of the at least three implantation tools (6) and a last exit to discard the non-desired follicles (7). The main advantage in this embodiment is the fact that the tools in each arm operate simultaneously and less effort is required to be applied on hair follicles.

The apparatus has, for this embodiment, preferably three extraction tools and three implantation tools that act together. The implantation system has incorporated therein the information regarding the number of follicles containing 1, 2 or 3 hairs, to implant and what are the respective regions for implantation. Thus the morphological organization of hair follicles in the implantation system simultaneously with the capacity of its mechanical arm to implant up to 100 follicles, allows for an extraordinary reduction of time necessary for intervention. Additionally, with the system of the present invention, the time of anaesthesia is reduced to about 4 minutes. The mechanical arms of robotic apparatus are preferably positioned at an angle of 180° between them. One of the arms comprises the instruments for extracting the follicles (14)—and the other arm comprises instruments for implantation (15) of the follicles, allowing the transplant procedure (extraction and implant) to be performed in a sequential manner or alternatively by a set of follicles.

In a second embodiment, the present invention comprises an apparatus for extracting, selecting and implanting hair follicles in which each tube or channel of the tool has the respective hose connected to a stationary ring (10) (either an extraction tool, implantation tool, or for collecting non desired hair follicles). Another mobile ring (11), which is associated to several capsules in the same manner as in the first embodiment, completes the system, as can be seen from FIG. 4, in which the second ring moves according to the operator's need, in order to collect and distribute the hair follicles through the desired tubes or channels, allowing for an effective distribution and with fewer moving parts. The mobile ring has more capsules than in the first embodiment, in order to be able to collect more follicles, while distributing already collected follicles, provided that the configuration is done in an appropriate manner. The main advantage in this embodiment is that it only requires a single engine to accomplish the collection and distribution of hair follicles, which leads to a smaller volume and less energy requirements. However, if follicles are considered to be not viable, or if the collected follicles are not all from the same type, the ring makes the collection and distribution individually but still, with the necessary speed to make it possible to reduce considerably the time of intervention.

On the arm of the extraction tool a tube is associated with the intermediate system represented in FIGS. 3 and 4. These, on the other hand, are connected through other tubes to the tubes or channels of the implantation tool (and, if the follicle is damaged, to the waste collector) allowing for rapid transportation and implantation of the extracted follicles. This intermediate system is located in the central support box of the apparatus of the present invention, avoiding the use of external extra elements, allowing to maintain a compact volume.

According to a third embodiment, the automated apparatus for hair transplant comprises a mechanical arm associated with a tool (FIG. 10) for extracting, selecting and implanting hair follicles comprising at least one cylindrical internal tube or cannula for collecting follicles and at least one external cylindrical concentric tube or cannula for puncturing the patient's skin, wherein the tool has a dual function of simultaneous extraction and implantation from 1 to 100 hair follicles.

In a preferred embodiment, the system has three or more tools of excision and/or implantation, with the movement of the same running in semi-independent manner, being possible that the speed of mechanical arms in the order of 360°, allowing the tools to cover a wider area of intervention (it is possible to work only in the section of follicles with one hair, or cover more than one section, thanks to the freedom of movement provided by the tools and the system of central distribution of the present invention). The tools to use in at least one articulated mechanical arm may be identical or different.

The possibility of associating acupuncture with anaesthesia is applicable to any embodiment of the present invention, because this minimizes the discomfort resulting from infiltration of anaesthetic solution in the patient's body and reduces the formation of edema.

In any embodiment of the present invention, the pressure exerted when introducing the follicles is controlled and monitored by the effort made by robot, being that when the pressure exceeds a pre-set threshold, a sound and visible alarm or warning is triggered, in order to ensure the safety and comfort of the patient, as well as to prevent the expulsion of the follicles previously implanted. The system of the present invention is controlled by a central industrial computer highly reliable, with a simple graphical interface and high usability. The system of the present invention gives audible alarms in the event of relevant changes occurring to the health and well-being of the patient and/or that may compromise the success of the intervention and the corresponding results, such as for example, a change in the vital signs or malfunctioning of the equipments. The present invention also provides for a system of remote access and control, whenever it is necessary and justifiable to monitor and control the procedure remotely.

Regarding the analysis system to the patient's scalp and hair follicles, both analysis can be carried out in real time, before and during the extraction, using the sensors present in the extraction and implantation tools of the present invention. However, if during the performed and recorded tests the analysis of follicles before and/or during the extraction procedure is unsatisfactory and/or insufficient, can optionally occur during the transition of the follicle from the extraction tool to the implantation tool.

One of the advantages and priorities in the present invention was to allow a proper hygiene or disposal of all the system's elements that come into contact with hair follicles, in order to avoid contamination on the following intervention (channels, capsules, needles, etc.).

According to an additional embodiment, it is expected that the joint use, with at least one of the systems herein disclosed, of a chair with rotary and directed motion (FIG. 5). The chair of FIG. 5 includes a system of rotation with several axis, adapting perfectly to the stages of hair follicle extraction and implantation with the present invention.

a) Pre-Transplant Evaluation

The pre-transplant system contemplates a unit for automatic calculation of the area of baldness and the number of follicles necessary to cover this area, with varying hair densities. This unit contains an algorithm for optimization that resets the number of differentiated follicles in the same area and that will serve as input for the extraction system. The simulation of both, differential implant scheme and predicted final result for the transplant, can be visualized in 3D mode on a regular monitor.

In the preoperative phase a preliminary assessment of the number of follicles required of each type (1, 2, 3 or more hair) carried out to obtain a satisfactory result, in accordance with the scheme of differential implantation visualized by users according to FIG. 9; this pre-operative evaluation or assessment can be done remotely, through the system of the present invention.

b) Extraction and Implantation of Hair Follicles

When the hair follicle extraction and implantation tools are separated, an incision is performed by external tubes or cannulas of the extraction tools and then the extraction occurs by suction/aspiration through multiple channels (24), with the aid of a vacuum system associated with, and the routing of the follicles is done directly to the channels of implantation, which may implant up to 100 follicles at each time. These multiple channels through which the hair follicles traverse allow that, in the passage of extraction for the implantation tool, they are positioned with the bulb on the proximal end of the implanting tool, i.e. in the front (considering the direction of implantation). The advantage of this procedure is the correct implantation of the hair follicles in the scalp through the bulb (root), that is, positioned in such a way as to encourage the growth of the hair.

The extraction tool in these embodiments comprises at least one cylindrical internal tube or cannula (19) for collecting the hair follicles and at least one external cylindrical concentric tube or cannula (20) for puncturing the skin and the tool for hair follicle implantation comprises at least one needle and at least one cylindrical adjacent tube (21) containing the, at least one, follicle to implant.

The screening of the hair follicles that contain 1, 2, 3 or more hairs and the morphological analysis can be made in real time, during the transplant, to assess what are the follicles that can be implanted on the front line in intermediate areas, in the back line, and so forth (FIG. 9).

The platform 1 integrates a computational system of simulation based on the input of data and growth analysis, cell differentiation and proliferation, with advanced techniques and enzyme analysis.

There are growth stimulating substances and others that work as inhibitors. For diagnosing the causes for lack of hair, for example, male pattern baldness, hair loss, miniaturization of hair, delay and interruption of hair growth, among other causes, it is necessary to proceed to the histochemical/enzymatic analysis of the follicles from different areas of the scalp (e.g., 50 to 100 in each area), identifying the substances involved and the corresponding receptors that, at that moment, influence the growth cycle of the hair.

This assessment was carried out during the transplant, is extremely beneficial to the patient, to the extent that it provides a diagnostic and curative treatment at the same time, opening up the possibility to appropriate preventive treatment to(s) its cause(s) of absence of hair.

A visualization system is included to carry out the analysis of the hair's density, counting of the number of follicles needed to implant as a function of the desired density and area. The visualization system performs after extraction a second morphological analysis to the following characteristics of the hair follicle: dysmorphic and fragile bulb, opaque, disruptive.

Platform 2 allows the administration of anaesthesia in various parts of the patient's head and through the simultaneous use of needles (12) (FIG. 6), with a centralized supply pump with pressure control (through a peristaltic valve (13), with rotation control, pressure and flow, allowing to administer the anaesthesia in approximately 4 to 5 minutes.

Currently the period for administering the anaesthesia is approximately 30 minutes in an area of approximately 180 $cm^2$, and preferably uses 27G sub-cutaneous needles 0.4×13 mm with syringes of 3.0 mL. Usually, one injection is applied at each time. On the other hand, the anaesthesia is administered in 2 distinct moments: 1) Anaesthesia of the donor area, followed by the extraction of the hair follicles; 2) anaesthesia of the receiving area, followed by the implantation of the same.

Platform 3 for extraction and implantation of hair follicles comprises a robotic system with multiple mechanical articulated arms (preferably with delta mechanical heads, due to its dynamic characteristics that allow high speed and accuracy of positioning), significantly reducing the positioning time for extraction and implantation of follicles and a system of rotary positioning which allows the orientation of heads as a function of the direction of the hair follicle to remove. The robotic apparatus has a mechanism for control and detection of the effort and pressure exerted by the arm of the robotic apparatus, as a guarantee of safety and well-being of the patient.

Until now, the unchanged positioning time during the transplantation was excessive causing great discomfort to the patient. During the extraction, the patient was accommodated in the prone position with the face fitted into a hole on the rolling bed, non-adjustable, extremely uncomfortable for many patients. The patient was forced to remain in this position for approximately 2.5 to 3 hours. In the implantation phase the position adopted is often the supine position, also uncomfortable after the first 20 minutes, and the patient is required to remain in the same position for approximately 2.5 to 3 hours. This limitation led into the convenient administration of benzodiazepine, as muscle relaxant.

As one can see from FIG. 6, the system of the present invention has three or more tools of excision and/or implantation, wherein the movement is semi-independent, being possible to rotate the mechanical arms and heads 360°, allowing for the mentioned tools to cover a wider area of intervention (it is possible to work only in the section of follicles containing one hair, or to cover more than one section, thanks to the freedom of movements provided by the tools and the system of central distribution of the present invention).

It is important to mention that the tools to use in both heads of both mechanical arms, according to one of the embodiments of the present invention, will be different, and in other embodiments, the same mechanical head accumulates both extraction and implantation functions.

The positioning and orientation of the robot are guaranteed by artificial vision (FlowVision), defining the ideal trajectory to be done as a function of the previous hair follicle, optimizing and reducing the overall time of the extraction and implantation procedure. The vision system allows for the recognition of follicles, performing on the first phase a morphological analysis to their general characteristics, identifying and selecting the viability of extraction for a later implantation. The vision system is also responsible for managing the positioning and orientation of the mechanical heads on the robot of the present invention.

The hair follicle extraction system comprises, in a preferred embodiment, 4 extraction tools. One of the tools of the present invention has a fixed position (master tool reference) with the possibility of performing a small orientation as a function of the hair follicle to excise and independently from the position and orientation of the mechanical head on the arm of the robot. The positioning and orientation of the central mechanical head of the robot are performed as a function of the master tool. The remaining 3 tools should allow for an adjustment of their positioning in relation to the master tool and as a function of the position of the hair follicles. An adjustment of orientation is made as a function of the orientation of the remaining 3 follicles to excise in order to ensure the required spacing and orientation between mechanical tools and the hair follicles to remove. The auxiliary tools for extraction will also have the possibility to carry out a rearward movement, whenever it is not necessary or not possible to perform the lateral movement of positioning as a function of the set of follicles to excise. The extraction of the follicles is performed by aspiration by reducing the physical contact with the hair follicles preventing its degradation.

The implantation is performed, preferably, with intervals of 4 mm between the follicles and to the extent that the transplant procedure takes place, the implantation tools retract up to 2 mm on the same alignment, so that the implanted hair follicles have, by the end of the intervention, a preferred relative minimum distance of 2 mm.

In case hair is detected on a location intended for hair follicle implantation, through the optical visualization system, the needle or tube/cannula corresponding to the implantation in this location retracts and does not perform the implant.

The system of the present invention has an integrated cleaning system for blood residues and loose hair rods, in the area of intervention and performs automatic and strict sterilization between transplants.

The sterilization proof in critical areas of the equipment of the present invention may be issued at any time, fetching the date and time at which the transplant procedure took place and/or through the patient's data.

Advanced safety systems are integrated in the system and apparatus of the present invention for protection of all parties involved in the procedure.

DETAILED DESCRIPTION OF THE INVENTION

Figure 1:
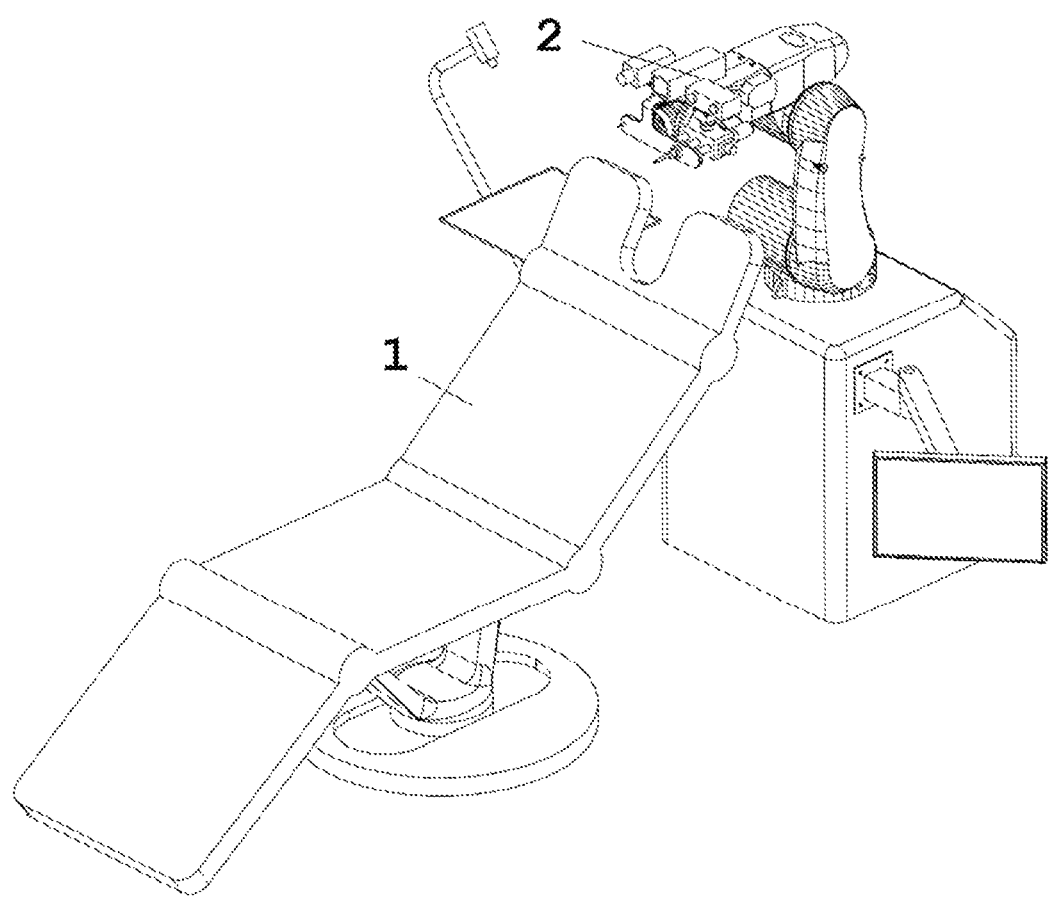
FIG. 1—Overview of Robotic Apparatus for Differentiated Hair Transplant: 1) Multi-Position Chair; 2) External Artificial Vision System, equipped with Scanning Laser, Time-of-Flight Camera and Conventional Cameras.
Figure 2:
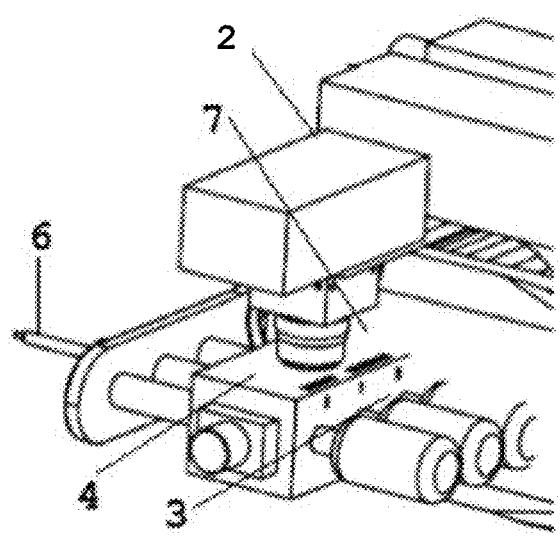
FIG. 2—Embodiment with the morphological separation system of hair follicles (3) including a selector system of hair density (4), equipped with a system of artificial vision (2) and needles/tubes/cannulas for hair follicle implantation (6) 1, 2 or 3 and a deposit for the rejected hair follicles (7).
Figure 3:
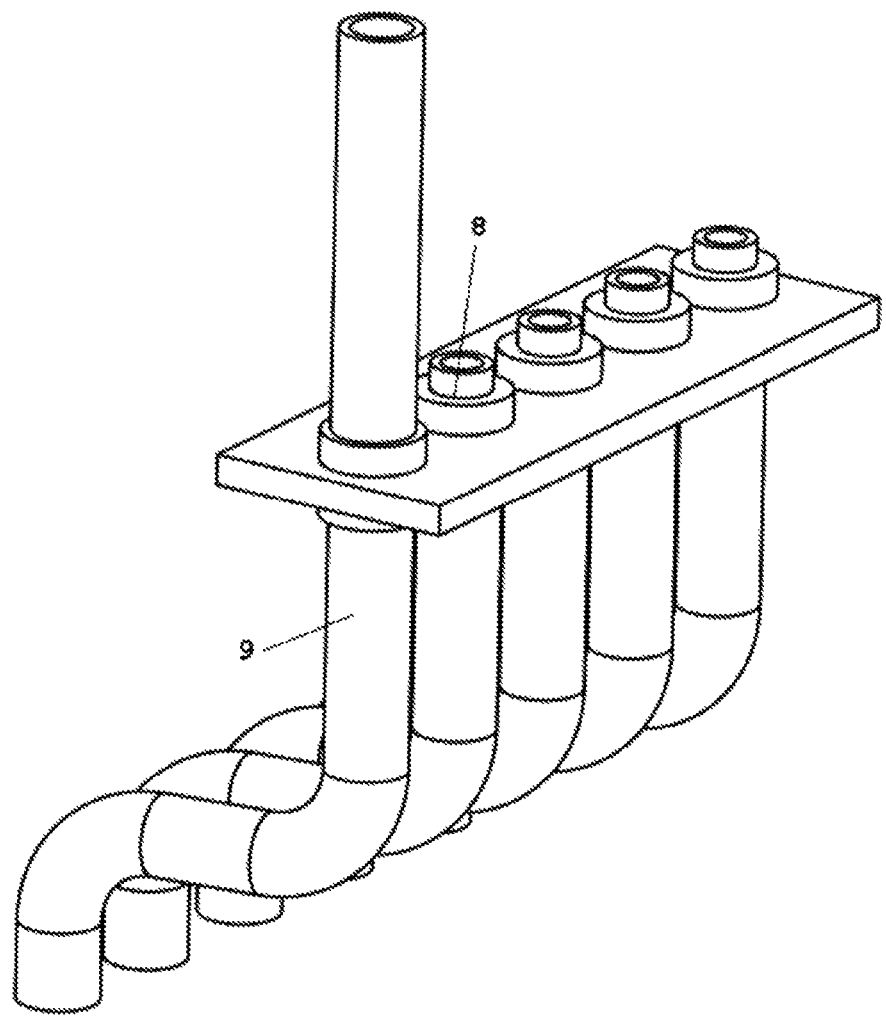
FIG. 3—Mechanical system to change the capsule nozzle (8) connected to the tubes/needles/cannulas for extraction and implant of hair follicles, through a hose (9).
Figure 4:
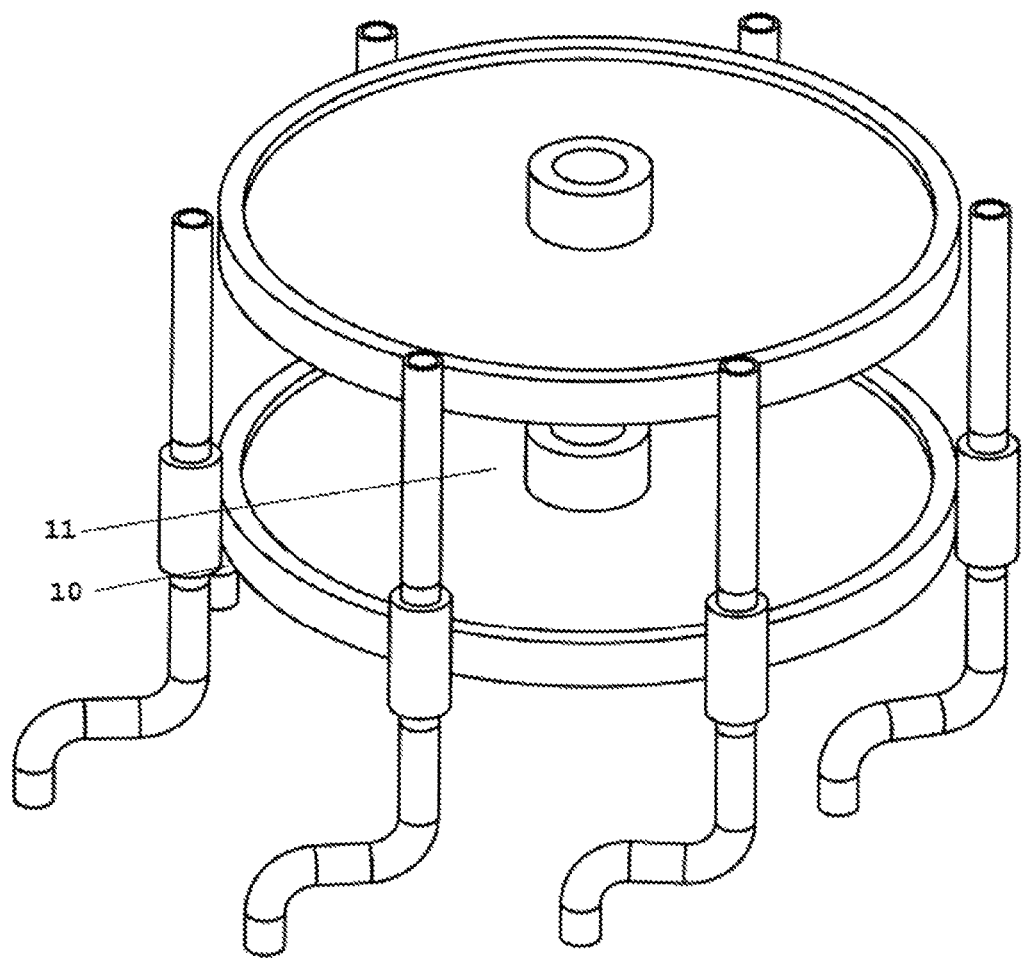
FIG. 4—Each tube/needle/cannula has its respective hose connected to a static ring (10). A second movable ring (11), where capsules are associated to, moves according to the what is needed, in order to collect and distribute the hair follicles through the desired tubes.
Figure 5:
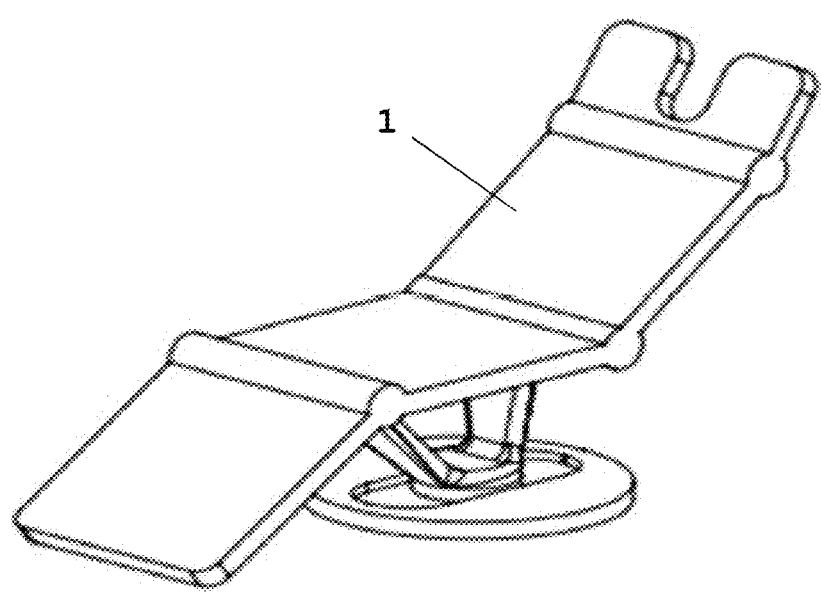
FIG. 5—chair with dynamic positioning (1).
Figure 6:
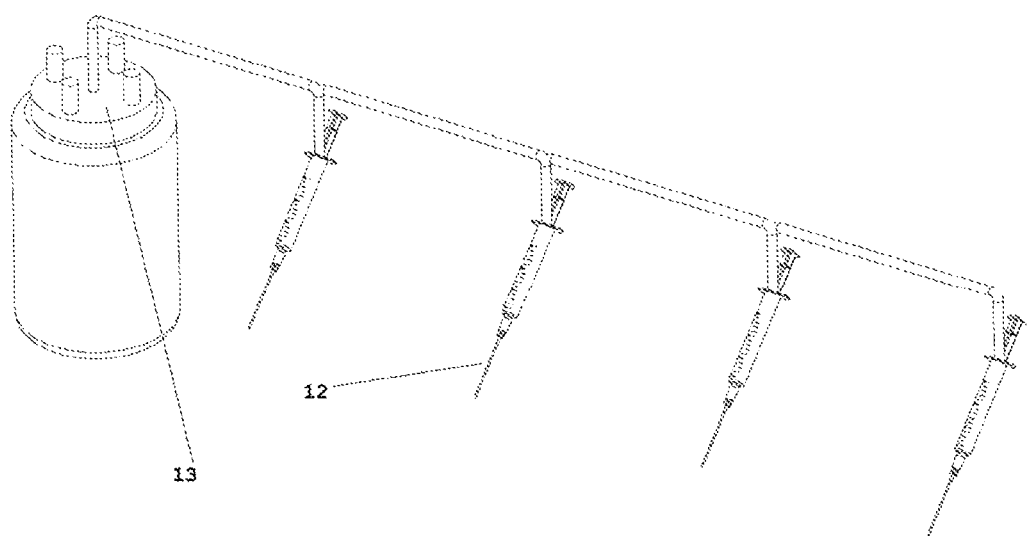
FIG. 6—Embodiment with 4 needles used for anaesthesia (12), with a centralized supply pump with pressure control through a peristaltic valve (13), with rotation, pressure and flow control.
Figure 7:
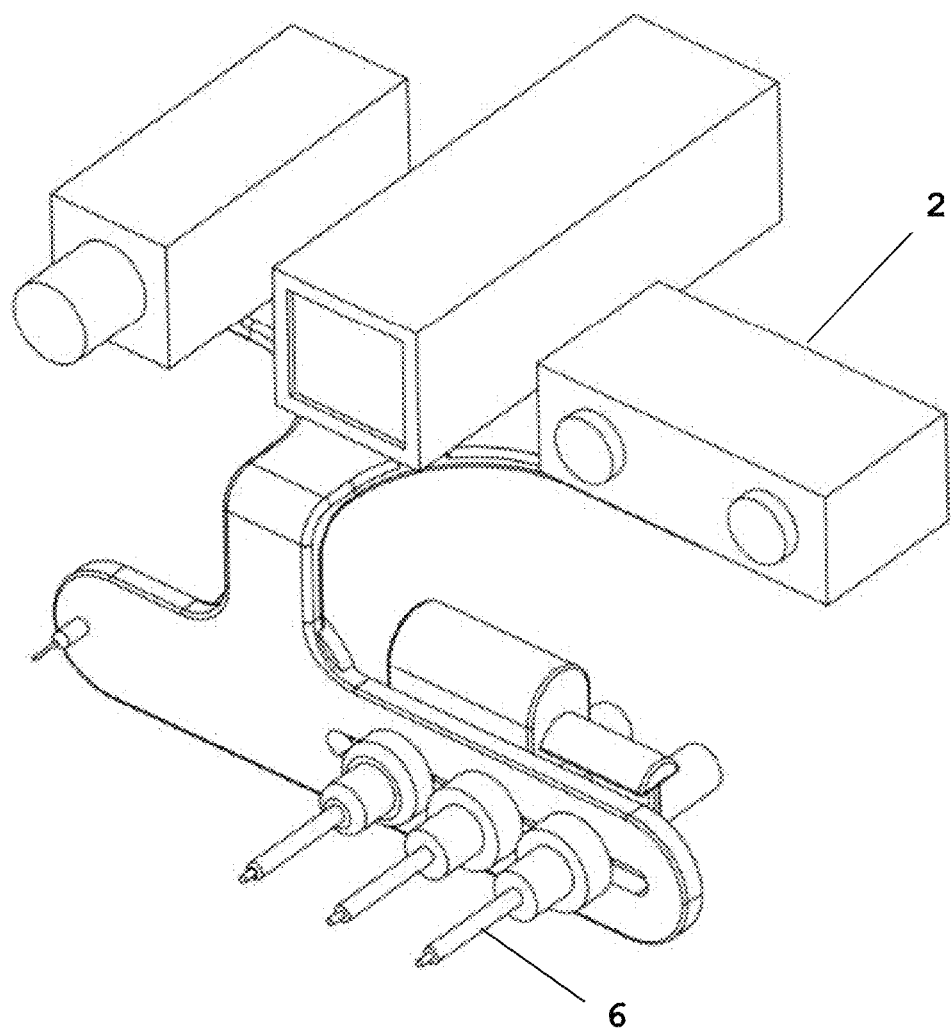
FIG. 7—positioning system of the hair follicles extraction and implantation tools.
Figure 8:
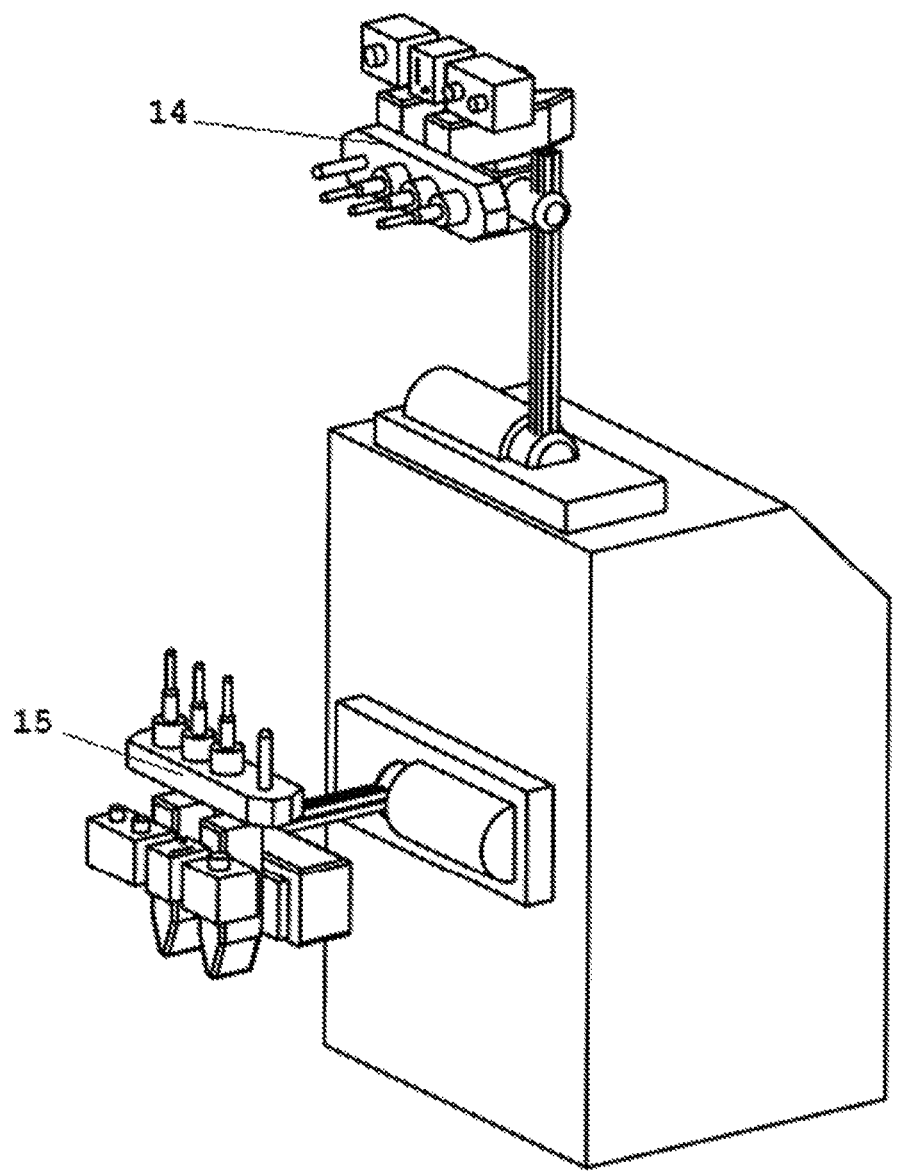
FIG. 8—Relative location of mechanical arms for extraction (14) and implantation (15).
Figure 9:
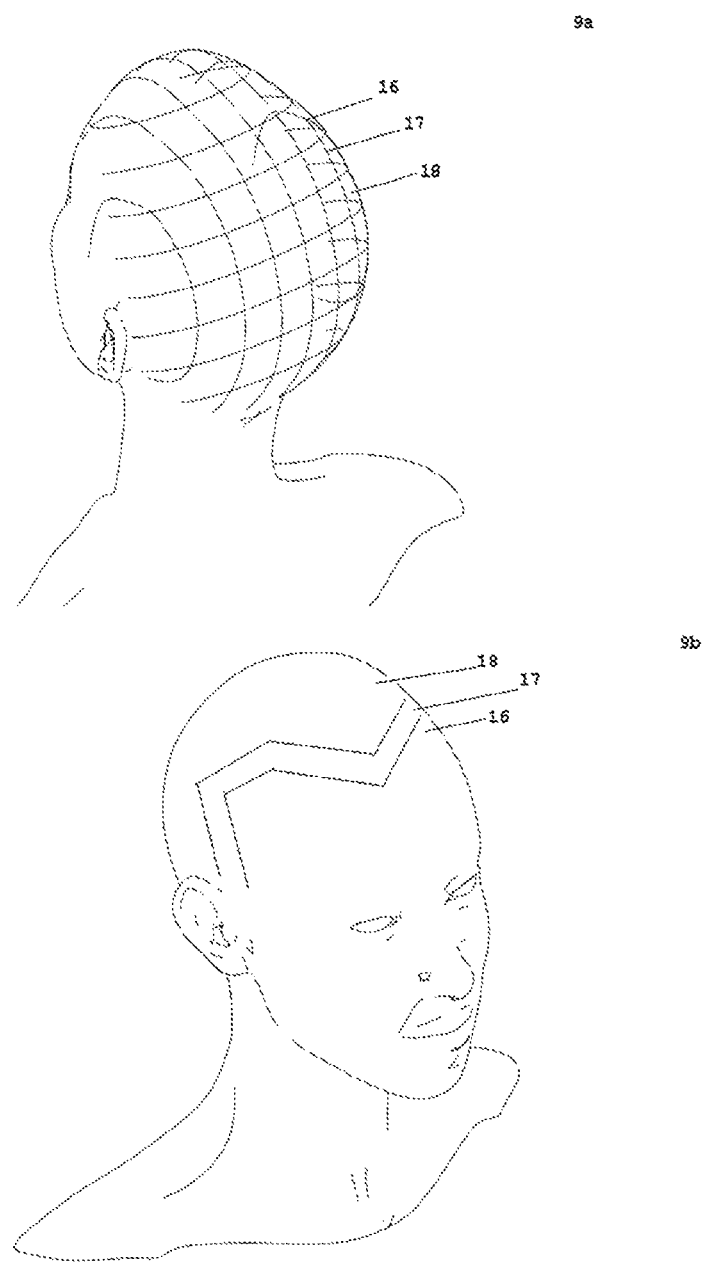
FIG. 9—Obtained images through the pre-transplantation system by identifying the areas of the patient's head to perform differential implant of hair follicles containing 1 hair (16), hair follicles containing 2 hairs (17) and hair follicles containing 3 hairs (18), from top (9a) and front/side (9b) perspectives.
Figure 10:
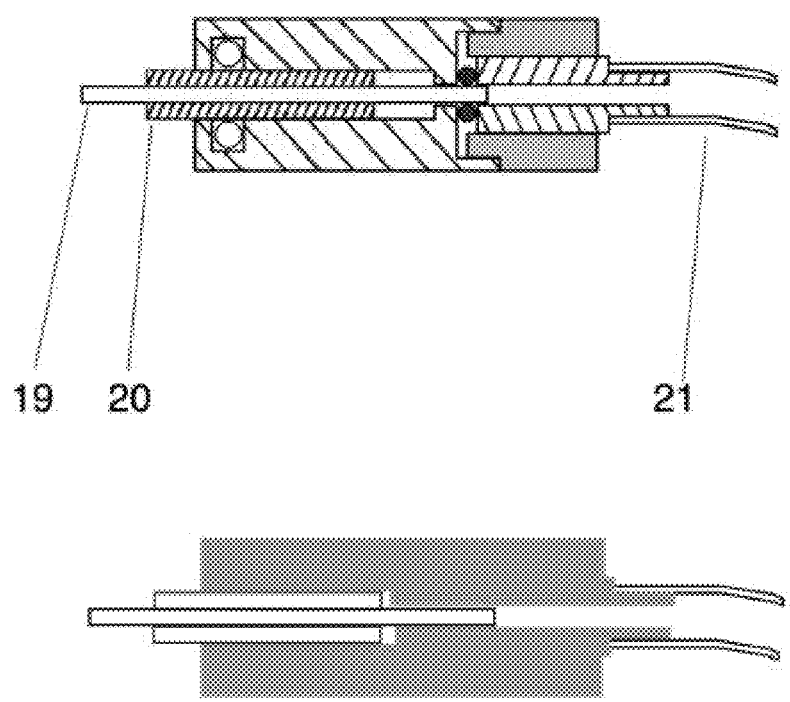
FIG. 10—Embodiment of the tool of the present invention with dual function of extraction and implantation of a hair follicle.
Figure 11:
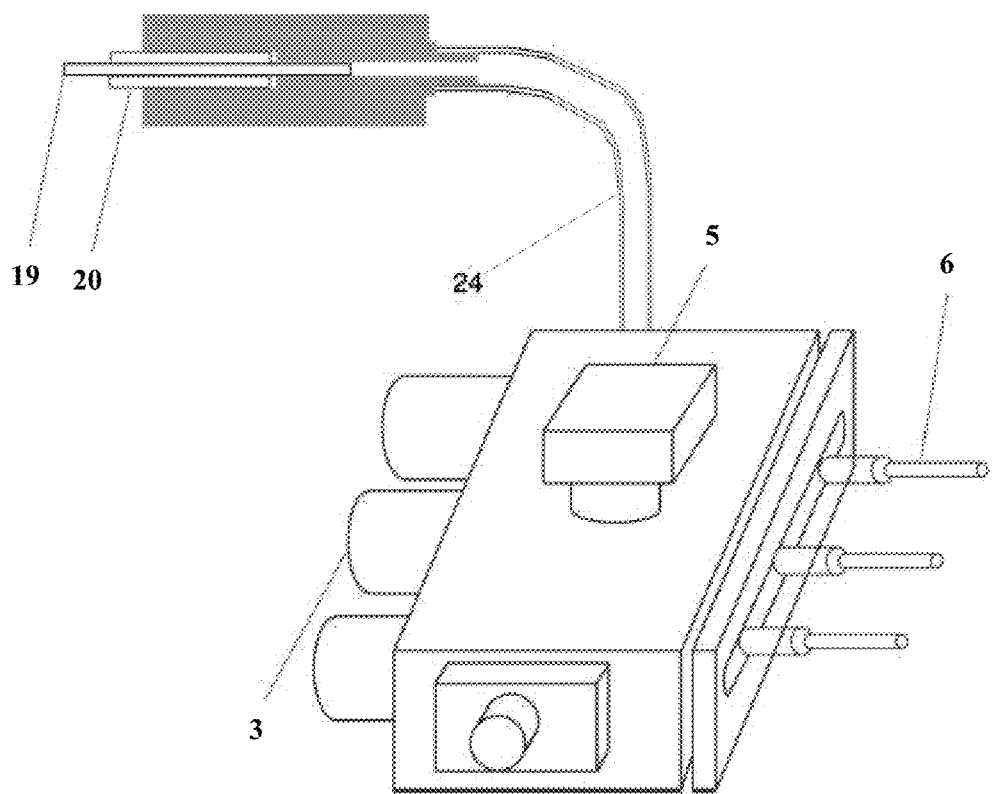
FIG. 11—Channel system with suction and vacuum (24) that extends from the extraction tool to the implantation tool (6).
Figure 12:
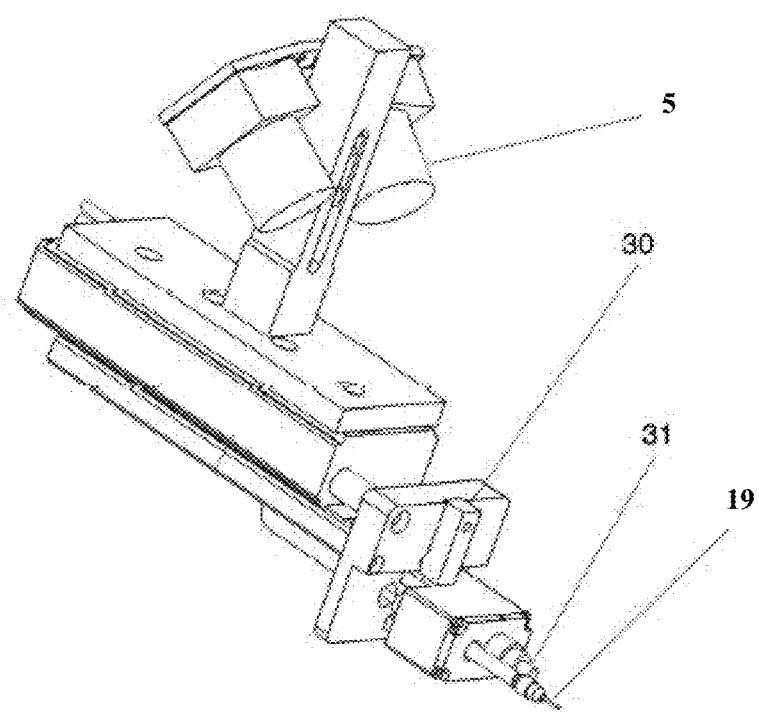
FIG. 12—Security mechanism with a sensor for monitoring the pressure exerted upon excision of the follicles (30) and a sensor for monitoring the distance to the patient's skin (31).

1. Programming of Robotic Tool 1.1—Introduction of information relating to the various possible pathologies of the scalp and respective treatments;
1.2—Introduction of the full known clinical history of the patient.
1.3—Introduction of the acceptance ranges for the evaluated morphological parameters.
1.4—Validation of the patient's body weight and the medication and anaesthesia doses to administer;
1.5—Validation of acceptance ranges for the levels of the assessment parameters of the patient's vital signs.

2. Video Conference Consultation 2.1. The patient schedules the appointment of the consultation and attends the consultation online, preferably through the website http://www.saudeviavel.pt. In the tab "videoconference consultation" the clinical form is completed with the patient's relevant personal data and the patient's clinical information, the payment information and scheduling options for the next appointment.

2.2. The entity providing the appointments introduces the name of the physician or technician responsible for conducting the consultation.

The clinical history of the patient is enquired and introduced in the system of the present invention.

2.3. During the consultation, a detailed observation of the head area is performed, with the purpose of evaluating the condition and state of development of the patient's baldness and also investigating the most appropriate solution for the patient's case, comprising or not a transplant procedure.

On this preoperative phase a preliminary assessment of the number of follicles required of each type (1, 2 or more hairs) is carried out to obtain a satisfactory result (depending on the mapping of differential implant); this preoperative assessment can be done remotely (stereoscopic base—not new/macroscopic) or in person.

For example, if the patient has total trichotomy at the time of preoperative assessment, it is possible to estimate the number of follicles vs. hairs in the donor area, assess whether they are sufficient to cover the area of implantation and predict with greater accuracy the final result; The system of pre-transplant contemplates a unit of automatic calculation of the area of baldness and the number of follicles needed to cover this area. This unit contains an algorithm for optimization that resets the number of differentiated follicles in the same area and that will serve as input for the extraction system. The simulation can be visualized in 3D mode on a monitor.

Results of Pre-Transplant Consultation

At the end of the appointment the result is translated into:
a. "With indication" for transplant or
b. "Counter-indication" for transplant by FUE and/or topical treatment.

The system sequentially suggests, through monitor visualization, the most adequate treatment(s) and treatment(s) plan, drawn up by the responsible technician.

Data Registration and Recording

The collected and recorded information, resulting from the query, is used in constructing a 3D map, showing the contours and dimensions of the patient's head and the exact location of the hair follicles, allowing to identify the existing hair follicles in the patients's scalp, to remove; the 3D map enables further definition of the ideal paths to be carried out by the system and apparatus of the present invention, during the transplant, being able to position itself correctly in relation to the preferred hair follicles and the extraction of the same.

Anaesthesia

The administration of anaesthesia is performed at the same time, preferably by 4 needles, in previously validated doses in the programming of the robotic system.

Transplantation

The implantation system has incorporated therein the information on the number of hair follicles containing 1 (16), 2 (17) or 3 (18) hairs to implant and corresponding regions defined in the pre-assessment phase.

The robot has an integrated communication system between the patient and the technician, allowing them to be in the same room or in separate rooms.

Names of the main responsible physician and technician, as well as the remaining relevant staff, the date, time, and chronometer, should be properly introduced in the system.

The visualization system and circuit integrates video and photographic cameras.

The patient's hair should be cut very short before the procedure, with the aid of a machine, with comb 0 and the head surface should be disinfected with povidone-iodine foam or other suitable substance.

It is preferably used, associated to the system and apparatus of the present invention, a Trendelenburg® chair or other adequate supporting means.

The anaesthesia is localized and through administrating Lidocain Hydrochloride (Xilonibsa® 2% with Epinephrine). A dilution of 60 $cm^3$ of NaCl0.9% solution is used for each dosage unit of anaesthesia (10 tubes). The maximum daily dose is 7 mg per kg. Each tube contains 1.8 mL corresponding to 31.14 mg, i.e. each dosage unit of anaesthesia contains 311.4 mg.

The needles for the administration of anaesthesia are thin; for example, size 27G "subcutaneous". The needles are introduced simultaneously in the scalp with an angle less than 90° for accomplishing a wider distribution of the anaesthetic. Aspirate before injecting with the purpose of avoiding any risk of intra-vascular administration.

The implantation follows the orientation guide of the remaining hairs to comply with the direction, angle and depth of implantation. The positioning and orientation of the robot are guaranteed by artificial vision (FlowVision), defining the ideal trajectory to be done as a function of the previous hair follicle, optimizing and reducing the overall time period of the extraction and implantation procedure.

The artificial vision system allows for the recognition of hair follicles, performing on a first phase a morphological analysis to their general characteristics, identifying and selecting the viability of extraction for a later implantation.

The vision system is responsible for managing the positioning and orientation of the robot's head, to perform the extraction of the hair follicles. The visualization system performs after extraction a second morphological analysis to the following characteristics of the hair follicle: dysmorphic and fragile bulb, opaque, disruptive.

The implantation is performed, preferably, with intervals of 4 mm between the follicles and to the extent that the transplant procedure takes place, the implantation tools retract up to 2 mm on the same alignment, so that the implanted hair follicles have, by the end of the intervention, a preferred relative minimum distance of 2 mm.

The system of the present invention has an integrated cleaning system for blood residues and loose hair rods, in the area of intervention and performs automatic and strict sterilization between transplants.

The sterilization proof in critical areas of the equipment of the present invention may be issued at any time, fetching the date and time at which the transplant procedure took place and/or through the patient's data.

The invention claimed is:

1. An automated apparatus for hair transplantation of at least one hair follicle, comprising a robot with at least one articulated mechanical arm and adapted to be positioned perpendicularly and adjacently in relation to a patient's head, comprising in association with the mechanical arm:
   (i) a tool assembly for differentially extracting, selecting and implanting the at least one hair follicle with administration of local and phased anaesthesia, and
   (ii) a computerized interface for analysis of hair follicles, through artificial vision,
   wherein the tool assembly comprises an extraction tool and an implantation tool, wherein the extraction tool comprises at least one cylindrical internal tube for collecting the hair follicles and at least one external cylindrical concentric tube for puncturing the skin and the implantation tool comprises at least one needle and at least one cylindrical adjacent tube containing the at least one hair follicle to implant; and
   wherein a channel system with suction and vacuum for selectively conducting hair follicles extends from the extraction tool to the implantation tool.

2. The apparatus according to claim 1, wherein the tool assembly has a dual function of simultaneous extraction and implantation from 1 to 100 hair follicles.

3. The apparatus according to claim 1, comprising a first mechanical arm associated with the extraction tool and a second mechanical arm associated with the implantation tool, wherein the mechanical arms are positioned with a relative angle of 180° between them.

4. The apparatus according to claim 1, wherein the extraction and implantation tools operate simultaneously and integrate a security mechanism with a sensor for monitoring the distance to the patient's skin and a sensor for monitoring the pressure exerted upon excision of the follicles, associated with a peristaltic valve with a vacuum system.

5. The apparatus according to claim 1, wherein pre-implantation separation and selection of hair follicles are based on real-time analysis of morphological characteristics, including thickness, length, typology and viability of the follicles.

6. The apparatus according to claim 1, wherein an audible and bright alarm is triggered when a programmed limit value for the exerted pressure is exceeded, when a change occurs in a patient's vital signs and in the event of malfunctioning of the apparatus.

7. The apparatus according to claim 1, wherein the apparatus is operated manually and remotely.

8. A method of hair transplantation using the apparatus according to claim 1, comprising using the apparatus for differentially extracting, selecting, and implanting at least one hair follicle with administration of local and phased anaesthesia.

9. The method according to claim 8, wherein the procedure comprises pre-analysis with assessment, screening, mapping of extraction and implantation points and simulation of cell growth of hair follicles with (i) computerized interface for online use and morphological analysis of hair follicles in real time, through artificial vision; (ii) system of local, global, simultaneous and phased sequential anaesthesia; and (iii) excision and sequential implantation of multiple follicles, preferably up to 100 follicles, wherein the follicles are selected and separated when excised and differentially implanted or eliminated.

10. The method according to claim 8, wherein during transplantation, the implantation of hair follicles is carried out in a sequential or simultaneous mode with the extraction of the follicles and differentially, by type of follicle, containing 1, 2, 3 or more hairs, and according to programmed morphological parameters of acceptance on the apparatus's computerized interface.

11. The method according to claim 8, wherein an incision is made by 3 tubes or needles at the same time, being the excision of the follicle performed through cylindrical transparent and disposable capsules with 0.75, 0.80 or 1.0 mm in diameter, by suction through multiple channels and a routing of the follicles is done directly, in an automated and differential way, into the channels and tubes or needles of implantation, and can implant up to 100 follicles at each time.

12. The method according to claim 8, wherein an anaesthesia is administered in low and appropriate doses according to the weight of the patient, in a time interval less than or equal to 4 minutes, using at least 4 needles simultaneously.

13. The method according to claim 12, wherein the administered anaesthesia is associated with acupuncture.

14. The method according to claim 8, wherein the implantation is performed with intervals of distance of 4 mm between each two follicles and the tubes or needles retract up to 2 mm on the same alignment, so that the implanted follicles have, in the end of the intervention, a relative preferred minimum distance of 2 mm.

* * * * *